United States Patent
Wang et al.

(10) Patent No.: US 10,799,672 B2
(45) Date of Patent: Oct. 13, 2020

(54) CATHETER BODY STRUCTURAL SUPPORT MEMBER INCLUDING A POLYMER HYPOTUBE

(71) Applicant: Covidien LP, Mansfield, MA (US)

(72) Inventors: Edwin Wang, Tustin, CA (US); Komonn Lim, Lake Forest, CA (US); Bryant Pham, Santa Ana, CA (US)

(73) Assignee: COVIDIEN LP, Mansfield, MA (US)

( * ) Notice: Subject to any disclaimer, the term of this patent is extended or adjusted under 35 U.S.C. 154(b) by 481 days.

(21) Appl. No.: 14/885,710

(22) Filed: Oct. 16, 2015

(65) Prior Publication Data

US 2017/0106166 A1    Apr. 20, 2017

(51) Int. Cl.
*A61M 25/00*    (2006.01)

(52) U.S. Cl.
CPC ...... *A61M 25/0052* (2013.01); *A61M 25/008* (2013.01); *A61M 25/0012* (2013.01); *A61M 25/0015* (2013.01); *A61M 25/0045* (2013.01); *A61M 25/0053* (2013.01); *A61M 25/0054* (2013.01); *A61M 25/0009* (2013.01); *A61M 2025/0059* (2013.01)

(58) Field of Classification Search
CPC .......... A61M 25/0012; A61M 25/0045; A61M 25/0053; A61M 25/005; A61M 2025/0047; A61M 25/0054
See application file for complete search history.

(56) References Cited

U.S. PATENT DOCUMENTS

| | | | |
|---|---|---|---|
| 4,385,635 A * | 5/1983 | Ruiz ................. | A61M 25/0045 600/435 |
| 6,050,949 A | 4/2000 | White et al. | |
| 6,387,075 B1 | 5/2002 | Stivland et al. | |
| 7,641,647 B2 | 1/2010 | Gunderson | |
| 7,678,075 B2 | 3/2010 | Wantink et al. | |
| 7,736,346 B2 | 6/2010 | Miller et al. | |
| 7,780,693 B2 | 8/2010 | Brady et al. | |
| 8,038,682 B2 | 10/2011 | McGill et al. | |
| 8,734,699 B2 | 5/2014 | Heideman et al. | |
| 8,814,825 B2 | 8/2014 | Tegg et al. | |
| 8,945,089 B2 | 2/2015 | Johnson et al. | |
| 8,951,225 B2 | 2/2015 | Evard et al. | |
| 2005/0283134 A1 | 12/2005 | Chan et al. | |
| 2007/0135763 A1* | 6/2007 | Musbach .......... | A61M 25/0054 604/96.01 |
| 2008/0188832 A1* | 8/2008 | Tanioka ................. | A61B 8/445 604/525 |
| 2009/0171300 A1 | 7/2009 | Parker et al. | |
| 2010/0023033 A1 | 1/2010 | Mauch et al. | |
| 2010/0087789 A1* | 4/2010 | Leeflang ............ | A61B 17/3207 604/265 |
| 2012/0123327 A1 | 5/2012 | Miller | |
| 2013/0253328 A1 | 9/2013 | Zelenka et al. | |

(Continued)

FOREIGN PATENT DOCUMENTS

| | | |
|---|---|---|
| CN | 101822867 A | 9/2010 |
| WO | 9601664 A1 | 1/1996 |

(Continued)

OTHER PUBLICATIONS

Llloyd, "So Many Polymers, So Little Time," Medical Plastics, Medical Device and Diagnostic Industry, Sep. 1, 2010, 4 pp.

(Continued)

*Primary Examiner* — Emily L Schmidt
(74) *Attorney, Agent, or Firm* — Shumaker & Sieffert, P.A.

(57) ABSTRACT

In some examples, a catheter body includes an outer jacket positioned over a structural support member. A proximal portion of the structural support member comprises a straight or tapered polymer hypotube and a distal portion of the structural support member comprises a distal support member that is more flexible than the polymer hypotube. In some examples, the polymer hypotube defines one or more openings, through which an adhesive may be introduced between the polymer hypotube and an inner liner of the catheter body.

21 Claims, 3 Drawing Sheets

(56) References Cited

U.S. PATENT DOCUMENTS

| | | | |
|---|---|---|---|
| 2014/0324093 A1 | 10/2014 | Chang et al. | |
| 2014/0336572 A1 | 11/2014 | Heisel et al. | |
| 2016/0067444 A1* | 3/2016 | Allen | A61M 25/0023 604/246 |
| 2016/0271362 A1* | 9/2016 | Van Liere | A61M 25/005 |
| 2017/0072163 A1* | 3/2017 | Lim | A61M 25/005 |

FOREIGN PATENT DOCUMENTS

| | | | |
|---|---|---|---|
| WO | 9633763 A2 | 10/1996 | |
| WO | 9917826 A1 | 4/1999 | |
| WO | 2014143198 A1 | 9/2014 | |

OTHER PUBLICATIONS

Hartford, "New Extrusion Techniques Advance Catheter Design," Extrusion, Medical Device and Diagnostic Industry, Feb. 20, 2013, 4 pp.

"euca AC, Technical details catheter," Innova, retrieved from http://innova-eg.com/eucatech/euca-ac#technical-specification on Feb. 23, 2015, 2 pp.

Extended European Search Report from counterpart European Application No. 16192450.1-1501, dated Mar. 14, 2017, 9 pp.

Examination Report from counterpart European Application No. 16192450.1, dated Apr. 29, 2020, 4 pp.

Response to Examination Report dated Apr. 29, 2020 from counterpart European Application No. 16192450.1, filed Jun. 3, 2020, 8 pp.

Communication under Rule 71(3) Intent to Grant dated Jul. 6, 2020 from counterpart European Application No. 16192450.1, 56 pp.

* cited by examiner

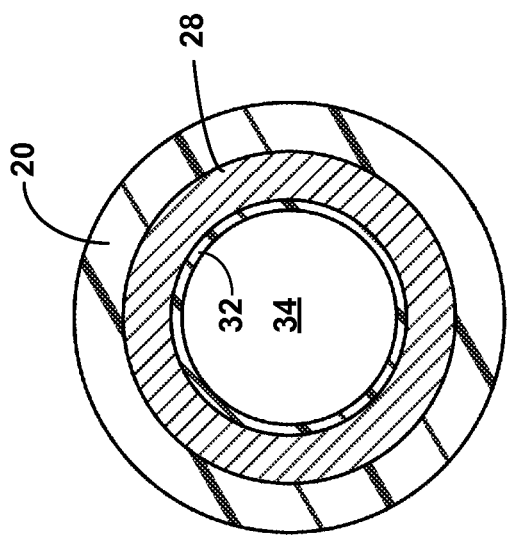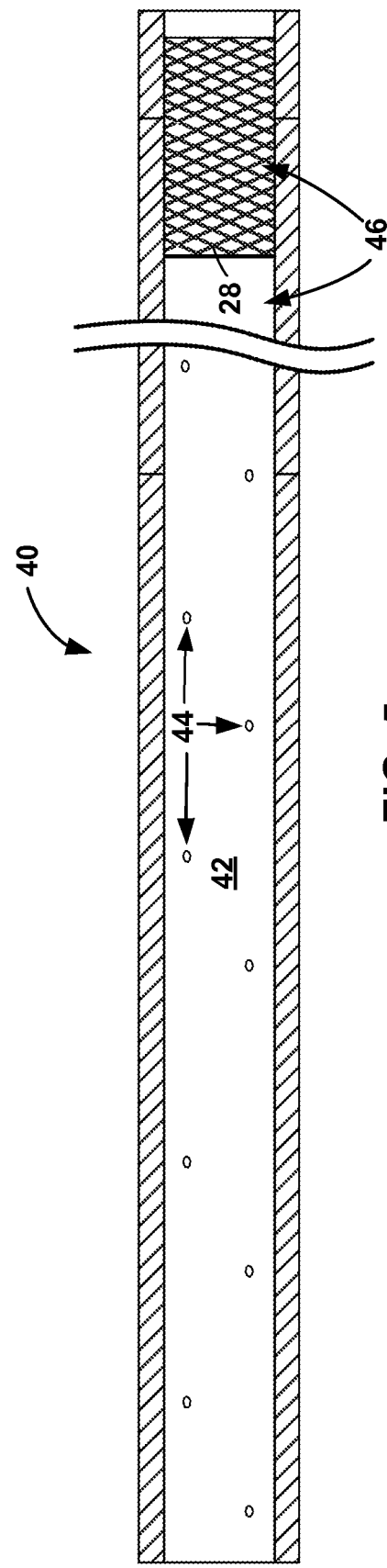

CATHETER BODY STRUCTURAL SUPPORT MEMBER INCLUDING A POLYMER HYPOTUBE

TECHNICAL FIELD

This disclosure relates to a medical catheter.

BACKGROUND

A medical catheter defining at least one lumen has been proposed for use with various medical procedures. For example, in some cases, a medical catheter may be used to access and treat defects in blood vessels, such as, but not limited to, lesions or occlusions in blood vessels.

SUMMARY

In some aspects, this disclosure describes example catheters, each catheter including a catheter body that includes an outer jacket positioned over a structural support member. A proximal portion of the structural support member comprises a straight or tapered polymer hypotube and a distal portion of the structural support member comprises a distal support member that is more flexible than the polymer hypotube. The distal support member can be, for example, a braided structure or a coil structure. The distal support member is longitudinally adjacent to the polymer hypotube. In some examples, a longitudinally extending wall of the polymer hypotube defines one or more openings, which facilitates the introduction of an adhesive between the polymer hypotube and an inner liner, which may be at least partially positioned within a lumen defined by the polymer hypotube. This disclosure also describes example methods of forming catheters and example methods of using catheters.

Clause 1: In some examples, a catheter comprises a catheter body comprising: a generally tubular outer jacket; and a structural support member positioned under said outer jacket, the structural support member having a proximal portion comprising a polymer hypotube and a distal portion comprising a distal support member that is more flexible than the polymer hypotube, wherein the distal support member is longitudinally adjacent to the polymer hypotube.

Clause 2: In some examples of the catheter of clause 1, the polymer hypotube comprises polyether ether ketone (PEEK).

Clause 3: In some examples of the catheter of clause 1 or clause 2, the polymer hypotube has a wall thickness of about 38.1 microns to about 63.5 microns.

Clause 4: In some examples of the catheter of any of clauses 1-3, the polymer hypotube has a stiffness of about 11.5 gram-force centimeter to about 460 gram-force centimeter.

Clause 5: In some examples of the catheter of any of clauses 1-4, the polymer hypotube extends along about 20% to about 50% of a total length of the catheter body.

Clause 6: In some examples of the catheter of any of clauses 1-5, the polymer hypotube has a length of about 80 centimeters to about 130 centimeters.

Clause 7: In some examples of the catheter of any of clauses 1-6, the polymer hypotube has a varying wall thickness.

Clause 8: In some examples of the catheter of clause 7, the polymer hypotube has a constant inner diameter and a varying outer diameter.

Clause 9: In some examples of the catheter of any of clauses 1-8, the polymer hypotube has a sidewall which is uncut along its length.

Clause 10: In some examples of the catheter of any of clauses 1-9, the structural support member comprises a braided member.

Clause 11: In some examples of any of clauses 1-10, the structural support member comprises a coil member.

Clause 12: In some examples of the catheter of clause 11, the coil member comprises at least one of nickel titanium or stainless steel.

Clause 13: In some examples of the catheter of any of clauses 1-12, the hypotube and the structural support member abut each other.

Clause 14: In some examples of the catheter of any of clauses 1-13, the outer jacket comprises a first outer jacket segment positioned over the polymer hypotube; and a second outer jacket segment adjacent to the first outer jacket segment and positioned over the distal support member.

Clause 15: In some examples of the catheter of any of clauses 1-14, the outer jacket comprises a single outer jacket extending over at least a portion of the polymer hypotube and at least a part of the distal support member.

Clause 16: In some examples, the catheter of any of clauses 1-15 further comprises an inner liner adjacent to the polymer hypotube, wherein the structural support member is positioned around the inner liner.

Clause 17: In some examples, the catheter of any of clauses 1-16 further comprises an inner liner, wherein the polymer hypotube is positioned around a proximal portion of the inner liner and the distal support member is positioned around a distal portion of the inner liner.

Clause 18: In some examples of the catheter of any of clauses 1-17, a longitudinally-extending wall of the polymer hypotube defines a plurality of openings.

Clause 19: In some examples of the catheter of clause 18, the openings are symmetrically arranged relative to a longitudinal axis of the polymer hypotube Clause 20: In some examples of the catheter of clause 18, the openings are asymmetrically arranged relative to a longitudinal axis of the polymer hypotube.

Clause 21: In some examples of the catheter of any of clauses 18-20, the openings each have a diameter of about 0.1 millimeters to about 0.8 millimeters.

Clause 22: In some examples of the catheter of any of clauses 18-21, the openings are distributed along a length of the polymer hypotube.

Clause 23: In some examples of the catheter of any of clauses 18-22, the longitudinally-extending wall of the polymer hypotube defines only two openings.

Clause 24: In some examples of the catheter of any of clauses 18-23, the catheter body further comprises: an inner liner defining an inner lumen of the catheter, wherein the polymer hypotube is positioned over at least a portion of the inner liner; and an adhesive positioned between at least a portion of the inner liner and at least a portion of the polymer hypotube, wherein the adhesive extends at least partially through at least one opening of the plurality of openings.

Clause 25: In some examples of the catheter of clause 24, the adhesive comprises at least one of polyether block amide or cyanoacrylate.

Clause 26: In some examples of the catheter of any of clauses 1-23, the catheter body further comprises: an inner liner defining an inner lumen of the catheter, wherein the polymer hypotube is positioned over at least a portion of the inner liner; and an adhesive positioned between at least a portion of the inner liner and at least a portion of the polymer hypotube.

Clause 27: In some examples, the catheter of any of clauses 1-26 further comprises a hub connected to the polymer hypotube, wherein the polymer hypotube is positioned between the structural support member and the hub.

Clause 28: In some examples of the catheter of any of clauses 1-27, the proximal portion of the catheter body is devoid of a braided structural support member or a coil structural support member.

Clause 29: In some examples, a catheter comprises a catheter body comprising: an inner liner defining an inner lumen of the catheter; a polymer hypotube positioned over at least a portion of the inner liner, wherein a longitudinally-extending wall of the polymer hypotube defines a plurality of openings; and an adhesive positioned between at least a portion of the inner liner and at least a portion of the polymer hypotube, the adhesive extending at least partially through at least one opening of the plurality of openings.

Clause 30: In some examples of catheter of clause 29, the polymer hypotube is positioned over a proximal portion of the inner liner, the catheter body further comprising a structural support member positioned over a distal portion of the inner liner, the structural support member being more flexible than the polymer hypotube and distal to the polymer hypotube.

Clause 31: In some examples of the catheter of any of clauses 29-30, the polymer hypotube extends along about 20% to about 50% of a total length of the catheter body.

Clause 32: In some examples of the catheter of clauses 29-31, the polymer hypotube has a stiffness of about 11.5 gram-force centimeter to about 460 gram-force centimeter.

Clause 33: In some examples of the catheter of clauses 29-32, the openings are symmetrically arranged relative to a longitudinal axis of the polymer hypotube.

Clause 34: In some examples of the catheter of clauses 29-32, the openings are asymmetrically arranged relative to a longitudinal axis of the polymer hypotube.

Clause 35: In some examples of the catheter of clauses 29-34, the openings are generally circular.

Clause 36: In some examples of the catheter of clauses 29-35, the openings each have a diameter of about 0.1 millimeters to about 0.8 millimeters.

Clause 37: In some examples of the catheter of clauses 29-36, the longitudinally-extending wall of the polymer hypotube defines only two openings.

Clause 38: In some examples of the catheter of clauses 29-37, the adhesive comprises at least one of polyether block amide or cyanoacrylate.

Clause 39: In some examples, a method of forming a catheter comprises positioning a polymer hypotube and a structural support member adjacent to each other along a longitudinal axis, the structural support member being more flexible than the polymer hypotube; and positioning an outer jacket over the polymer hypotube and the structural support member, wherein a proximal portion of the catheter comprises the polymer hypotube and a distal portion of the catheter comprises the structural support member.

Clause 40: In some examples of the method of clause 39, positioning the polymer hypotube and the structural support member adjacent to each other comprises: positioning an inner liner over a mandrel; positioning the polymer hypotube over a proximal portion of the inner liner; and positioning the structural support member over a distal portion of the inner liner adjacent to the polymer hypotube.

Clause 41: In some examples, the method of clause 40 further comprises positioning an adhesive between the inner liner and the polymer hypotube.

Clause 42: In some examples of the method of any of clauses 39-41, positioning the polymer hypotube and the structural support member adjacent to each other comprises abutting the polymer hypotube and the structural support member.

Clause 43: In some examples of the method of any of clauses 39-42, positioning the outer jacket over the polymer hypotube and the structural support member comprises heat shrinking the outer jacket over the polymer hypotube and the structural support member.

Clause 44: In some examples of the method of any of clauses 39-43, positioning the outer jacket over the polymer hypotube and the structural support member comprises: positioning a first outer jacket segment positioned over the polymer hypotube; and positioning a second outer jacket segment adjacent to the first outer jacket segment and over the structural support member.

Clause 45: In some examples of the method of any of clauses 39-44, positioning the outer jacket over the polymer hypotube and the structural support member comprises positioning a single outer jacket extending over at least a portion of the polymer hypotube and at least a portion of the structural support member.

Clause 46: In some examples, the method of any of clauses 39-45 further comprises plurality of openings in a longitudinally-extending wall of the polymer hypotube.

Clause 47: In some examples of the method of clause 46, the openings are generally circular.

Clause 48: In some examples of the method of clause 46 or clause 47, the openings each have a diameter of about 0.1 millimeters to about 0.8 millimeters.

Clause 49: In some examples of the method of any of clauses 46-48, defining the plurality of openings comprises laser drilling the plurality of openings in the longitudinally-extending wall of the polymer hypotube.

Clause 50: In some examples of the method of any of clauses 46-49, the openings are symmetrically arranged relative to a longitudinal axis of the polymer hypotube.

Clause 51: In some examples of the method of any of clauses 46-49, the openings are asymmetrically arranged relative to a longitudinal axis of the polymer hypotube.

Clause 52: In some examples of the method of any of clauses 46-51, the openings are distributed along a length of the polymer hypotube.

Clause 53: In some example, the method of any of clauses 46-51 further comprises, after defining the plurality of openings: introducing an inner liner into the polymer hypotube; and introducing an adhesive between the polymer hypotube and the inner liner through at least one opening of the plurality of openings.

Clause 54: In some examples of the method of clause 53, the adhesive comprises at least one of polyether block amide or cyanoacrylate.

Clause 55: In some examples of the method of clause 53 or clause 54, introducing an adhesive between the polymer hypotube and the inner liner through at least one opening of the plurality of openings comprises injecting the adhesive through the at least one opening with a syringe.

Clause 56: In some examples, a method comprises introducing a catheter body into a patient, the catheter body comprising: a generally tubular outer jacket; and a structural support member positioned under said outer jacket, the structural support member having a proximal portion comprising a polymer hypotube and a distal portion comprising a distal support member that is more flexible than the polymer hypotube, wherein the distal support member is longitudinally adjacent to the polymer hypotube. The method further comprises guiding a distal end of the catheter body to a treatment site within the patient.

Clause 57: In some examples, the method of clause 56 further comprises introducing a guidewire in a patient, wherein guiding the catheter body to a treatment site within the patient comprises guiding the catheter body to the treatment site over the guidewire.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF THE DRAWINGS

FIG. 3 is conceptual cross-sectional view of the catheter body of FIG. 1 taken along line A-A in FIG. 1.

FIG. 4 is a conceptual cross-sectional view of the catheter body of FIG. 1 taken along line B-B in FIG. 1.

FIG. 5 is a partial cutaway view of another example catheter body, with part of the outer jacket removed.

DETAILED DESCRIPTION

Figure 1:
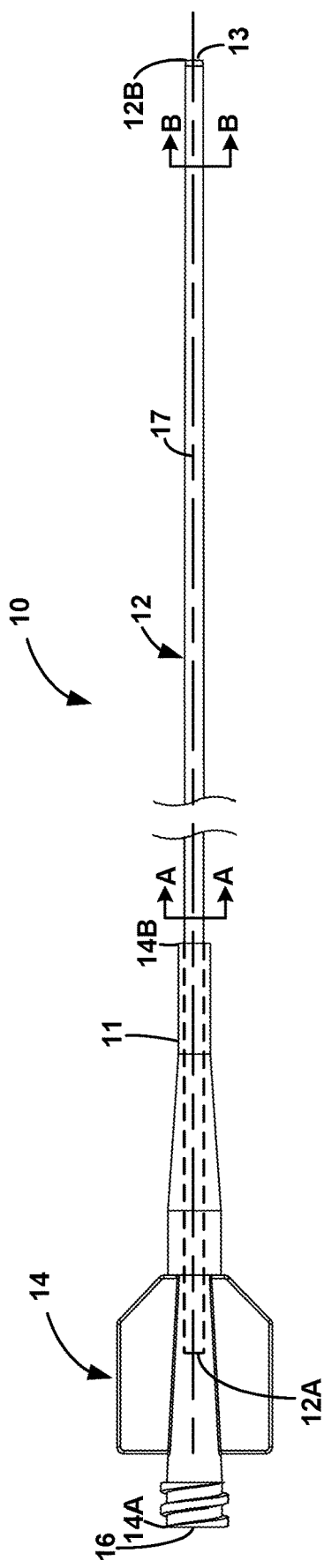
FIG. 1 is a side elevation of an example catheter, which includes a hub and a catheter body including a structural support member, a proximal portion of the structural support member comprising a polymer hypotube and a distal portion of the structural support member comprises a distal support member that is more flexible than the polymer hypotube.

In some examples, a medical catheter ("catheter") described herein includes a structural support member and an outer jacket positioned over the structural support member. A proximal portion of the structural support member comprises a polymer hypotube and a distal portion of the structural support member comprises a distal support member that is more flexible than the polymer hypotube. The distal support member can include, for example, a coil member defining a coil structure (e.g., a helical coil structure), a braided member, or any combination thereof. The structural support member is configured to exhibit a varying stiffness ranging from a relatively stiff proximal portion to a relatively flexible distal portion. This stiffness profile of the structural support member, and, consequently, the catheter body, may allow for easier navigation 0(e.g., steering and manipulation) of the catheter body through vasculature of a patient compared to a catheter body including a structural support member having continuous stiffness along its entire length. For example, the polymer hypotube may provide the catheter body with sufficient structural integrity (e.g., columnar strength) to permit the catheter body to be advanced through the vasculature from a pushing force applied to a proximal section of the catheter body, without undesirable compression or bending (e.g., kinking) of the catheter body, while the distal portion may provide the catheter body with sufficient flexibility to lead the catheter body through vasculature, e.g., tortuous vasculature in a brain of a patient.

The stiffness of the polymer hypotube may help increase the pushability and torqueability of the catheter body, e.g., compared to a catheter body that has coil member or a braided member at a proximal portion of a structural support member. In some examples, the polymer hypotube may better transmit torques to the distal section of the catheter body, and may be more resistant to kinking upon rotation of the catheter body from the relatively proximal section of the catheter body compared to catheters that have a coil member or a braided member at a proximal portion of a structural support member. Better torqueability and pushability may contribute to easier navigability of the catheter body, e.g., through tortuous vasculature in a brain of the patient.

The catheters described herein may be advanced to a target tissue site (or "target location") within vasculature of the patient in cooperation with a guidewire, an inner catheter, or both, which may aid in the navigation of the catheter through the vasculature. For example, an inner lumen of the catheter body may be configured to receive a guidewire or an inner catheter, such that the catheter body may be guided through vasculature over the guidewire or the inner catheter. In other examples, the catheters described herein may help guide another catheter to a target location within the vasculature, e.g., the catheters may be configured to be received in a lumen of another catheter.

FIG. 1 is a side elevation view of an example catheter 10, which includes catheter body 12 and hub 14. Catheter hub 14 is positioned at a proximal end of catheter 10 and defines an opening 16 through which an inner lumen of catheter body 12 may be accessed and, in some examples, closed. For example, catheter hub 14 may include a luer connector for connecting to another device, a hemostasis valve, or another mechanism or combination of mechanisms. In some examples, catheter 10 includes strain relief member 11, which may be a part of hub 14 or may be separate from hub 14. In other examples, the proximal end of catheter 10 can include another structure in addition or, or instead of, hub 14.

Catheter body 12 is a flexible elongated body that extends from proximal end 12A to distal end 12B and defines at least one inner lumen (e.g., one inner lumen, two inner lumens, or three or more inner lumens) that terminates at distal opening 13 defined by catheter body 12. In some examples, the flexible catheter body 12 is configured to substantially conform to the curvature of the vasculature when introduced in the vasculature. In the example shown in FIG. 1, proximal end 12A of catheter body 12 is received within hub 14 and is mechanically connected to hub 14 via an adhesive, welding, or another suitable technique or combination of techniques. Opening 16 defined by hub 14 and located at proximal end 14A of hub 14 is aligned with the inner lumen of catheter body 12, such that the inner lumen of catheter body 12 may be accessed via opening 16.

Catheter body 12 has a suitable length for accessing a target tissue site within the patient from a vascular access point. The length may be measured along longitudinal axis 17 of catheter body 12. The target tissue site may depend on the medical procedure for which catheter 10 is used. For example, if catheter 10 is a distal access catheter used to access vasculature in a brain of a patient from a femoral artery access point at the groin of the patient, catheter body 12 may have a length of about 129 centimeters (cm) to about 135 cm, such as about 132 cm, although other lengths may be used.

Although primarily described as being used to reach relatively distal vasculature sites, the catheters described herein may readily be configured to be used with other target tissue sites. For example, the catheters may be used to access tissue sites throughout the coronary and peripheral vasculature, the gastrointestinal tract, the urethra, ureters, Fallopian tubes and other body lumens.

Figure 2:
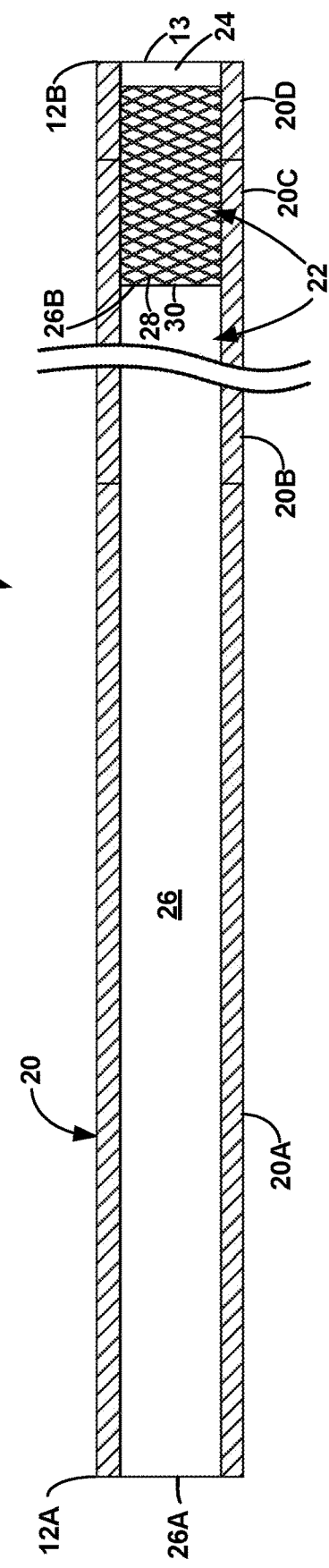
FIG. 2 is a partial cutaway view of the catheter body of FIG. 1, with part of the outer jacket removed.

FIG. 2 is a side elevation, partial cutaway view of catheter body 12, and illustrates catheter body 12 with a part of outer jacket 20 removed. Thus, outer jacket 20 is shown in cross-section, the cross-section being taken along longitudinal axis 17. In addition to outer jacket 20, catheter body 12 includes structural support member 22 and radiopaque marker 24. Outer jacket 20 is positioned over structural support member 22. Although not shown in FIG. 2, in some examples, catheter body 12 further comprises an inner liner (e.g., inner liner 32 shown in FIGS. 3 and 4), and structural support member 22 is positioned between the inner liner and outer jacket 20.

A proximal portion of structural support member 22 includes polymer hypotube 26 and a distal portion of structural support member 22 includes distal support member 28, which can be more flexible than polymer hypotube 26. Distal support member 28 is positioned adjacent to polymer hypotube 26 and may, in some examples, be directly adjacent to polymer hypotube 26 (e.g., in abutting contact with polymer hypotube 26). For example, in the example shown in FIG. 2, polymer hypotube 26 and distal support member 28 define butt joint 30. Polymer hypotube 26 and distal support member 28 can be directly mechanically connected to each other in some examples, such as by an adhesive, by welding, or the like. In other examples, polymer hypotube 26 and distal support member 28 remain separate from each other and are not connected to each other. Although not shown in FIG. 2, in some examples, distal support member 28 may be spaced from polymer hypotube 26, such as by another support member or a gap may be defined between polymer hypotube 26 and distal support member 28. In still other examples, distal support member 28 can be omitted altogether.

Structural support member 22 is configured to increase the structural integrity of catheter body 12 while allowing catheter body 12 to remain relatively flexible. For example, member 22 may be configured to help catheter body 12 substantially maintain its cross-sectional shape or at least help prevent catheter body 12 from buckling or kinking as it is navigated through tortuous anatomy. Structural support member 22, together with the inner liner and outer jacket 20, may help distribute both pushing and rotational forces along a length of catheter body 12, which may help prevent kinking of catheter body 12 upon rotation of catheter body 12 or help prevent buckling of catheter body 12 upon application of a pushing force to catheter body 12. As a result, a clinician may apply pushing forces, rotational forces, or both, to a proximal portion of catheter body 12, and such forces may cause a distal portion of catheter body 12 to advance distally, rotate, or both, respectively.

One structural characteristic of catheter body 12 that may contribute at least to the pushability and compression resistance of the catheter body 12 is polymer hypotube 26. One structural characteristic of catheter body 12 that may contribute at least to the flexibility of catheter body 12 is distal support member 28. The material and configuration of distal support member 28 may provide the flexibility required for a clinician to track distal end 12B of catheter body 12 to a target tissue site.

Polymer hypotube 26 may be a substantially tubular (e.g., cylindrical or nearly cylindrical) body formed from any suitable polymer material, such as a thermoplastic elastomer. Examples of polymer materials from which polymer hypotube 26 may be formed include, but are not limited to, polyether ether ketone (PEEK), polyamide (such as Grilamid TR-55 (e.g., of durometer 85D), available from EMS-CHEMIE (North America) Inc. of Sumter, S.C. USA), polyester-ether block copolymer (such as Hytrel® 8238, available from E. I. du Pont de Nemours & Co. of Wilmington, Del. USA), copolyester (such as Tritan MX-731 (e.g., of durometer R115), available from Eastman Chemical Co. of Kingsport, Tenn. USA), polyethylene terephthalate glycol comonomer (such as Skygreen S-208, available from SK Chemicals America, Inc. of Irvine, Calif.), or high elastic polyurethane (such as Pellethane 2363 (preferably of durometer 75D), available from Lubrizol Advanced Materials, Inc. of Cleveland, Ohio USA. In some examples, polymer hypotube 26 can be a substantially solid polymer tube, e.g., having a sidewall that is substantially solid (e.g., solid or nearly solid or lacking any cuts or openings formed therein). In other examples, as described with respect to FIG. 5, a longitudinally extending wall of polymer hypotube 26 may define one or more openings, the longitudinally extending wall extending from proximal end 26A to distal end 26B of hypotube 26.

Polymer hypotube 26 extends along a proximal section of catheter body 12, and distal end 26B of polymer hypotube 26 is proximal to distal support member 28. The length of polymer hypotube 26 may be selected to provide catheter body 12 with the desired physical characteristics, e.g., columnar strength. In some examples, polymer hypotube 26 may extend along 20% to about 50% of a total length of catheter body 12. In some examples in which catheter 10 is configured to be used to access relatively distal tissue sites, e.g., in a brain of a patient, polymer hypotube 26 may have a length of about 80 cm to about 130 cm. However, polymer hypotube 26 may have other lengths in other examples. Polymer hypotube 26 may have a wall thickness of about 38.1 microns to about 63.5 microns, or about 50 microns, though other thicknesses may be used in other examples. The hypotube 26 may have a uniform wall thickness or a varying wall thickness, e.g. with a thicker wall in the proximal region and a thinner wall in the distal region. Such a varying wall thickness can be achieved, for example, by incorporating a constant inner diameter of the hypotube 26 with a larger outer diameter in the proximal region and a smaller outer diameter in the distal region; in such a case the outer diameter may taper gradually along some or all of the length of the hypotube, or in one or more tapering segments adjacent to one or more segments of constant outer diameter.

The physical characteristics of polymer hypotube 26 may provide catheter body 12 with pushability and resistance to compression, which in turn may aid a clinician's efforts to push catheter body 12 distally, e.g., past a curve in the vasculature. The stiffness of polymer hypotube 26 may be selected based upon the particular application for catheter 10. As an example, polymer hypotube 26 may have a mean stiffness of about 0.010 inch-pounds (about 11.5 gram-force centimeter) to about 0.40 inch-pounds (about 460 gram-force centimeter), such as about 0.018 inch-pounds (about 20.7 gram-force centimeter), about 0.030 inch pounds (about 34.6 gram-force centimeter), or about 0.333 inch-pounds (about 383.7 gram-force centimeter). In some examples, polymer hypotube 26 has stiffness than is less than a solid metal hypotube has a similar or identical thickness, but greater than a braided member or coil member having a similar or identical thickness. Polymer hypotube 26 may, therefore, provide higher columnar strength to catheter body 12 compared to a braided member or coil member at the proximal portion, but may be more flexible than a solid metal hypotube at the proximal portion. The higher flexibility may help improve the navigability of catheter body 12 through tortuous vasculature.

In addition, polymer hypotube 26 may exhibit better compression resistance than a metal hypotube that is cut, e.g., in a spiral pattern or another pattern. Polymer hypotube 26 may also be less expensive to produce than a cut metal hypotube. Laser cutting a metal hypotube may consume a relatively high amount of energy (power) and may take a relatively long period of time (e.g., 30 minutes per metal hypotube), which may translate to high component cost.

Polymer hypotube 26 may be formed any suitable technique. In some examples, polymer hypotube is manufactured by extruding the polymer material into the tubular body shape.

Distal support member 28 may comprise a structure other than a polymer hypotube. In some examples, distal support member 28 comprises a braided member, which may comprise a generally tubular braided or woven structure, a coil member, which may comprise one or more wires in a coil configuration (e.g., a helical configuration), or a combination of braided member and a coil member. The braided member and/or the coil member may be formed from any suitable material or combination of materials, such as, but not limited to nickel titanium (Nitinol), stainless steel, or another suitable metal or metal alloy. In examples in which distal support member 28 comprises a braided member, the braid may have any suitable pick count. In addition, in examples in which distal support member 28 comprises a coil member, the coil may define any suitable pitch. The pick count and pitch may be selected to provide the distal section of catheter body 12 with the desired flexibility.

Outer jacket 20 may comprise a generally tubular structure positioned over structural support member 22. Example materials from which outer jacket 20 may be formed include, but are not limited to, a thermoplastic elastomer material such as a block copolymer. In some examples, the block copolymer material used may comprise a polyether block amide (e.g., Pebax; a material commercially available from Arkema, Inc. of Blooming Prairie, Minn.). In some cases, the material forming outer jacket 20 may have mechanical properties that contribute to the tendency of catheter body 12 to exhibit both resistance to kinking and a desirable level of flexibility. The material forming outer jacket 20 may also provide desirable torque transference and thus assist with the transference of pushing or rotational forces from the proximal portion of catheter body 12 to the distal portion of catheter body 12.

In some examples, outer jacket 20 may comprise one segment extending over at least a portion of polymer hypotube 26 and at least a portion of distal support member 28. In other examples, outer jacket 20 may comprise more than one segment, e.g., one outer jacket segment may be positioned over polymer hypotube 26, and another outer jacket segment may be positioned over distal support member 28. However, a common outer jacket segment overlapping at least a portion of both polymer hypotube 26 and distal support member 28 may help improve the durability of the connection between the components of catheter body 12 and may help better distribute forces (e.g., pushing forces or torsional forces) from proximal end 12A of catheter body 12 to distal end 12B. For example, in examples in which polymer hypotube 26 and distal support member 28 are attached to each other, and in the event the attachment fails, the outer jacket segment encompassing and engaging with both polymer hypotube 26 and distal support member 28 may help maintain the relative positioning of the polymer hypotube 26 and distal support member 28.

FIG. 2 illustrates an example in which outer jacket 20 comprises a plurality of segments 20A-20D. Segments 20A-20D may comprise one or more materials exhibiting the same characteristics or exhibiting varying characteristics. For example, segments 20A-20D may comprise materials exhibiting varying durometer values, such that a more proximal segment of outer jacket 20 may exhibit a durometer value indicating greater hardness than a more distal segment of outer jacket 20. A variation in durometer value among segments of outer jacket 20 may contribute to the ability of catheter body 12 to transmit a desired force in a proximal to distal direction, while contributing to the flexibility required for a clinician to track distal end 10B of catheter 10 to a desired site of the vasculature.

The hardness of segments 20A-20D may be selected to obtain more or less flexibility, torqueability, and pushability for all or part of catheter body 12. For example, to help configure catheter body 12 to have a relatively stiff proximal section to increase the pushability of catheter body 12, and to include a relatively flexible distal section to allow catheter body 12 to traverse through tortuous vasculature, segment 20A may have a greater durometer than segment 20B, which may have a greater durometer than segment 20C, which may have a greater durometer than segment 20D. In this way, the outer jacket 20 may have a decreasing stiffness. Other stiffness profiles may also be used.

In some examples, catheter body 12 includes marker 24, which may be attached to (or embedded within, or sandwiched between) an inner liner of catheter body 12, structural support member 22, and/or outer jacket 20 using any suitable technique. Marker 24 is formed from a radiopaque material and may allow a clinician to determine the location of catheter body 12 within a patient via a suitable medical imaging technique. Example radiopaque materials include, but are not limited to, gold, platinum, tantalum, and combinations thereof. In some examples, outer jacket 20 is positioned over marker 24, which may help prevent an outer surface of marker 24 from being exposed. In the examples shown in FIG. 2, marker 24 is positioned between an inner liner and outer jacket 20. Marker 24 may be formed from any suitable material, may be radiopaque, and may be in the form of a continuous ring, a discontinuous ring, or multiple segments that extend around the perimeter of catheter body 12. In some examples, marker 24 may be positioned to indicate the location of the distal tip of catheter body 12 and, therefore, may be positioned proximate to distal opening 12B.

FIG. 3 is a conceptual cross-sectional view of a proximal section of catheter body 12 taken along line A-A in FIG. 1. As shown in FIG. 3, the proximal section of catheter body 12 includes inner liner 32, polymer hypotube 26, and outer jacket 20, polymer hypotube 26 being positioned between inner liner 32 and outer jacket 20. In some examples, polymer hypotube 26 is attached to one or both of inner liner 32 and outer jacket 20, such as by an adhesive (e.g., a thermoplastic plastic or thermoset plastic), by welding, or any combination thereof. An inner surface of polymer hypotube 26 can, in some examples, be roughened to aid in the attachment of inner liner 32 to the inner surface. In other examples, however, inner liner 32 may be attached to the inner surface of polymer hypotube 26 without roughening up the inner surface.

In other examples of catheter body 12, a relative position of polymer hypotube 26 and inner liner 32 is substantially fixed (e.g., fixed or nearly fixed) by outer jacket 20, which may form a relatively tight fit around hypotube 26 and hold hypotube 26 against inner liner 32 via friction. Thus, polymer hypotube 26 may be directly adjacent to one or both of inner liner 32 and outer jacket 20, or a layer of adhesive or another material may be positioned between polymer hypotube 26 and one or both of inner liner 32 and outer jacket 20.

Inner liner 32 defines inner lumen 34 of catheter body 12. In some examples, inner liner 32 extends from proximal end 12A of catheter body 12 to distal end 12B. In other examples, inner liner 32 may extend proximal to proximal end 12A of catheter body 12, e.g., and may attach to hub 14. Thus, inner lumen 34 defines a passageway extending at least from proximal end 12A of catheter body 12 to distal end 12B, terminating at opening 13 (FIGS. 1 and 2) Inner lumen 34 may be sized to receive a medical device (e.g., another catheter, a guidewire, an embolic protection device, a stent, an embolic coil, a thrombectomy device, a delivery system used with any of the foregoing, or any combination thereof), a diagnostic agent, a therapeutic agent, or the like. At least the inner surface of the inner liner 32 may be lubricious in some examples in order to facilitate the introduction and passage of objects through inner lumen 34. For example, the material from which the entire inner liner 32 is formed may be lubricious, or inner liner 32 may be formed from two or more materials, where the material that defines inner lumen 34 may be more lubricious than the material that interfaces with structural support member 22. In addition to, or instead of, being formed from a lubricious material, in some examples, an inner surface of inner liner 32 may be coated with a lubricious coating.

In some examples, however, catheter body 12 may not include inner liner 32, or inner liner 32 may only extend through a part of catheter body 12. For example, polymer hypotube 26 may define part of inner lumen 34, and inner liner 32 may only be present in a distal section of catheter body 12, e.g., inner liner 32 may be coextensive with distal support member 28, but not coextensive with polymer hypotube 26 or only partially coextensive with polymer hypotube 26. In these examples, polymer hypotube 26 may define a lubricious inner surface, e.g., the polymer material may be reinforced by inorganic particles or talc. Such a polymer hypotube 26 may define a sufficiently lubricious inner surface to facilitate the introduction of objects through inner lumen 34, thereby eliminating the need for inner liner 32 at least in the part of catheter body 12 including polymer hypotube 26. The elimination of inner liner 32 in at least a proximal section of catheter body 12 may help increase the diameter of inner lumen 34 for a given catheter body outer diameter.

FIG. 4 is a conceptual cross-sectional view of catheter body 12 taken along line B-B in FIG. 1. As shown in FIG. 4, the distal section of catheter body 12 includes inner liner 32, distal support member 28, and outer jacket 20, distal support member 28 being positioned between inner liner 32 and outer jacket 20. In some examples, distal support member 28 is attached to one or both of inner liner 32 and outer jacket 20, such as by an adhesive (e.g., a thermoplastic plastic or thermoset plastic), by welding, or any combination thereof. In other examples, distal support member 28 is secured in place, e.g., against inner liner 32, by outer jacket 20, which may form a relatively tight fit around distal support member 28. Thus, distal support member 28 may be directly adjacent to one or both of inner liner 32 and outer jacket 20, or a layer of adhesive or another material may be positioned between distal support member 28 and one or both of inner liner 32 and outer jacket 20.

The inner diameter of distal support member 28 may be selected such that distal support member 28 may be positioned over inner liner 32, e.g., in a relatively close fit. For example, the inner diameter of distal support member 28 may be substantially equal to or just slightly greater than the outer diameter of inner liner 32.

As discussed above, in some examples, a polymer hypotube of a structural support member may define one or more openings, which may facilitate the introduction of an adhesive between inner liner 32 (if present) and the polymer hypotube. FIG. 5 is a side elevation of an example catheter body 40, which is similar to catheter body 12 shown in FIG. 1, but includes polymer hypotube 42 defining a plurality of openings 44. In particular, catheter body 40 includes structural support member 46, where a proximal portion of structural support member 46 includes polymer hypotube 42 and a distal portion of structural support member 46 includes distal support member 28. Polymer hypotube 42 may be similar to polymer hypotube 26 shown in FIG. 2, but includes openings 44. In particular, a longitudinally extending wall of polymer hypotube 42 defines a plurality of openings 44, which may be symmetrically or asymmetrically arranged relative to a longitudinal axis of polymer hypotube 26. The longitudinally extending wall extends from proximal end 42A to a distal end 42B of polymer hypotube 42. Openings 44 differ from the openings at the proximal and distal ends 42, 42B of polymer hypotube 42.

Openings 44 may have any suitable distribution along a length of polymer hypotube 42. For example, openings 44 may be substantially evenly distributed (e.g., evenly distributed or nearly evenly distributed) along a length of polymer hypotube 42, or may be unevenly distributed. Depending on the viscosity of an adhesive introduced through openings 44, distributing openings 44 along the length of polymer hypotube 42, rather than just including openings 44 in one or limited locations, may help achieve better adhesion (e.g., more uniform adhesion) between inner liner 32 and polymer hypotube 42 by more thoroughly positioning adhesive between inner liner 32 and polymer hypotube 42.

In some examples, openings 44 are spaced from an adjacent opening 44 in a longitudinal direction by about 20 cm, although other longitudinal spacing is contemplated. In addition, openings 44 may be circumferentially aligned with another opening 44 in a circumferential direction, e.g., may be spaced from another opening 44 by about 90 degrees to about 180 degrees, although other circumferential spacing is contemplated. In other examples, openings 44 are offset from each other in a circumferential direction, such that no two openings 44 are circumferentially aligned.

Polymer hypotube 42 may define any suitable number of openings 44, such as one, two, three, or four or more openings. The number of openings 44 may affect the stiffness of polymer hypotube 42. Where relatively more openings 44 are present, polymer hypotube 42 may exhibit relatively less stiffness; where relatively fewer openings 44 in polymer hypotube 42 are present, polymer hypotube 26 may exhibit relatively greater stiffness. Although ten openings on one side of polymer hypotube 42 are shown in FIG. 5, polymer hypotube 42 may define additional openings on the side of hypotube 42 not shown in FIG. 5, or may define fewer openings.

Openings 44 can define any suitable shape and dimension. The shape and dimension of each opening 44 can be selected to configure openings 44 to receive an adhesive and/or adhesive introduction tool, yet small enough to prevent the adhesive from flowing back out of the opening 44. For example, openings 44 may each be circular in shape, and/or may each have a diameter of about 0.1 millimeters to about 0.8 millimeters. The dimension and distribution of openings 44 may be selected to maintain the structural integrity of polymer hypotube 42, e.g., the size of each opening 44 can be relatively small so as to maintain the columnar strength of polymer hypotube 42.

Openings 44 may be formed in polymer hypotube 44 using any suitable technique. In some examples, openings 44 are formed by laser drilling or by a mechanical drill. After drilling, polymer hypotube 42 may be cleaned, e.g., with alcohol, in order to remove any debris resulting from the drilling process.

In some examples, an adhesive may be introduced between inner liner 32 and polymer hypotube 42 via one or more openings 44. The adhesive can be, for example, a relatively low-viscosity adhesive, such as, but not limited to, a polyether block amide or cyanoacrylate. For example, a tip of a syringe (e.g., 21 gauge to 24 gauge syringe), or another suitable implement, may be introduced through a first opening 44, and the adhesive may be subsequently released from the syringe and into the space between inner liner 32 and polymer hypotube 42. If hypotube 42 defines one or more additional openings 44, the syringe may be moved to each of these other openings, and a user may introduce adhesive between inner liner 32 and polymer hypotube 42 via the additional one or more openings. Prior to being cured (e.g., by time, moisture, light, or heat), the adhesive may have a low enough viscosity to diffuse (e.g., flow) from opening 44 to the space under polymer hypotube 42 and between adjacent openings 44. Once cured, the adhesive may mechanically connect inner liner 32 and polymer hypotube 42.

The adhesive may, in some examples, extend at least partially through one or more openings 44. For example, the adhesive, once cured, may partially or completely seal one or more openings 44. The presence of cured adhesive at least partially within the openings 44 may help reduce any impact the openings 44 have on the stiffness of polymer hypotube 42.

Figure 6:
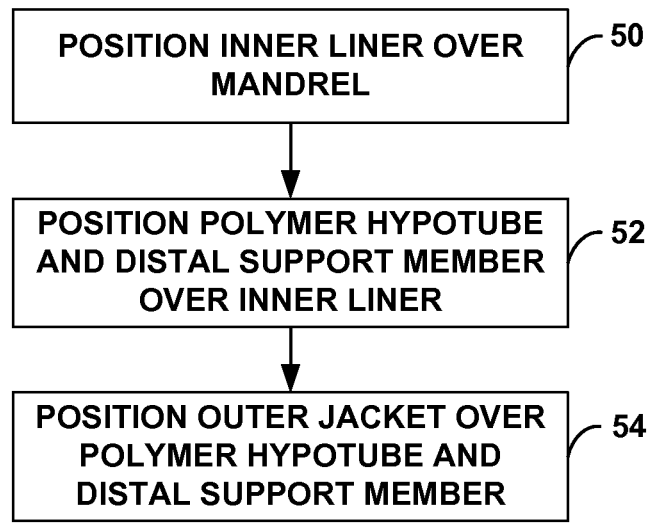
FIGS. 6 and 7 are flow diagrams of example methods of forming the catheters of FIG. 1 or 4.

The catheters described herein can be formed using any suitable technique. FIG. 6 is a flow diagram of an example method of forming a catheter including a structural support member, where a proximal portion of the structural support member includes a polymer hypotube and a distal portion of the structural support member includes a distal support member that is more flexible than the polymer hypotube. Although FIG. 6 is described with reference to catheter body 12 shown in FIGS. 1 and 2, in other examples, the technique shown in FIG. 6 may be used to form another catheter body.

In accordance with the techniques shown in FIG. 6, inner liner 32 may be positioned over a suitable mandrel (50), as by inserting the mandrel through an end of inner liner 32. As discussed above, in some examples, polymer hypotube 26 may define a part of inner lumen 34, and inner liner 32 may not extend through the entire polymer hypotube 26 or may not extend through any part of polymer hypotube 26. In these examples, the method shown in FIG. 6 may include positioning inner liner 32 over only a part of the length of the mandrel that corresponds to catheter body 12.

The mandrel may be formed from any suitable material. The material from which a suitable mandrel is formed may be configured to relatively easily release inner liner 32, e.g., after catheter body 12 is formed over the mandrel. For example, a mandrel may be formed from an extruded PTFE (e.g., a mandrel may consist of or consist essentially of an extruded PTFE). An extruded PTFE material may define a relatively lubricious outer surface, which may allow for relatively easy release of inner liner 32 from the mandrel, e.g., even in the absence of one or more additional lubricious coatings on the outer surface of the mandrel.

In some examples, after positioning inner liner 32 over the mandrel, inner liner 32 may be heat shrunk onto the mandrel and may, as a result, conform to the outer surface of the mandrel. Structural support member 22 may be positioned over inner liner 32 on the mandrel. For example, polymer hypotube 26 may be positioned over a proximal portion of inner liner 32, and distal structural support member 28 may be positioned over a distal portion of inner liner 32 adjacent to polymer hypotube 26 along a longitudinal axis (52). In some examples, positioning polymer hypotube 26 and distal support member 28 over inner liner 32 may comprise abutting polymer hypotube 26 and distal support member 28. In examples in which distal support member 28 comprises a coil member, the coil member may be wound around the distal portion of inner liner 32 or may be pushed onto the distal portion of inner liner 32. In examples in which distal support member 28 comprises a braided member, the braided member may be braided around the distal portion of inner liner 32 or may be pushed onto the distal portion of inner liner 32.

In examples in which inner liner 32 does extends only partially through polymer hypotube 26, the method shown in FIG. 6 may include positioning distal support member 28 over inner liner 32 and positioning polymer hypotube 26 over a proximal portion of inner liner 32. In examples in which inner liner 32 does not extend through polymer hypotube 26, the method shown in FIG. 6 may include positioning distal support member 28 over inner liner 32 and positioning polymer hypotube 26 adjacent to inner liner 32, e.g., in an abutting relationship. In some examples, the mandrel is configured such that an inner surface of polymer hypotube 26 and an inner surface of inner liner 32 are substantially aligned (e.g., aligned or nearly aligned) so the inner surfaces are substantially continuous in order to minimize or even eliminate any disruptions (e.g., protrusions or divots) along inner lumen 34. The disruptions may adversely affect the ease with which a medical device may be advanced through inner lumen 34.

In some examples, one or both of polymer hypotube 26 and distal support member 28 are not adhered to inner liner 32, but, rather, are held in place by a friction fit and are further secured in place by outer jacket 20. In other examples, however, one or both of polymer hypotube 26 and distal support member 28 may be adhered to inner liner 32. For example, an adhesive may be applied to inner liner 32 before positioning polymer hypotube 26 and/or distal support member 28 over inner liner 32. In other examples, as described with reference to FIG. 7, an adhesive may only be applied to the distal portion of inner liner 32, the portion corresponding to distal support member 28 before positioning polymer hypotube 26 and distal support member 28 over inner liner 32. An adhesive may then be introduced between polymer hypotube 26 and inner liner 32 using the technique described with respect to FIG. 7. In either of these examples, the adhesive can be, for example, a thermoplastic material or a thermoset material, such as a thermoset polymer and/or a thermoset adhesive (e.g., a thermoset polyurethane adhesive, such as Flexobond 430, commercially available from Bacon Industries of Irvine, Calif.).

As another example, an adhesive may be applied to one or both of polymer hypotube 26 and distal support member 28 after the one or both of polymer hypotube 26 and distal support member 28 are positioned on inner liner 32. For example, a thermoset or thermoplastic polymer may be introduced through openings defined by polymer hypotube 26 and/or openings defined by distal support member 28.

After structural support member 22 is positioned over inner liner 32, outer jacket 20 may be positioned over polymer hypotube 26 and distal support member 28 (54). In examples in which at least a portion of structural support member 22 is adhered to inner liner 32, the adhesive may be cured or at least partially cured prior to positioning outer jacket 20 over polymer hypotube 26 and distal support member 28. In other examples, however, adhesive may be fully cured after outer jacket 20 is positioned over polymer hypotube 26 and distal support member 28.

In some examples, positioning outer jacket 20 over polymer hypotube 26 and distal support member 28 may comprise positioning a single segment of outer jacket 20 over at least a portion of polymer hypotube 26 and at least a portion of distal support member 28. In other examples, positioning outer jacket 20 over polymer hypotube 26 and distal support member 28 may comprise positioning a first segment of outer jacket 20 over polymer hypotube 26, and positioning a second segment of outer jacket 20 adjacent to the first segment of outer jacket 20 and over distal support member 28. If more than two segments of outer jacket 20 are used, the remaining segments of outer jacket 20 may be placed adjacent to one another over portions of structural support member 22.

In some examples, outer jacket 20 may be formed from a heat shrinkable material. After outer jacket 20 is placed in position, heat may be applied to outer jacket 20 so as to heat-shrink outer jacket 20 over polymer hypotube 26 and distal support member 28. A heat shrink tube may be positioned over outer jacket 20, and heat may be applied to cause the heat shrink tube to wrap tightly around outer jacket 20. In examples in which outer jacket 20 comprises multiple segments, the heat and wrapping force may cause segments of outer jacket 20 to fuse together to define a substantially continuous outer jacket 20. The heat shrunk tube may then be removed from the assembly, e.g., via skiving or any suitable technique.

In some examples, the technique shown in FIG. 6 may include positioning marker 24 over inner liner 32, before positioning outer jacket 20 over polymer hypotube 26 and distal support member 28, or at least before positioning the distal segments of outer jacket 20 over polymer hypotube 26 and distal support member 28. In addition, hub 14 can be attached to proximal end 12A of catheter body 12 using any suitable technique, such as an adhesive, welding, or any combination thereof.

Figure 7:
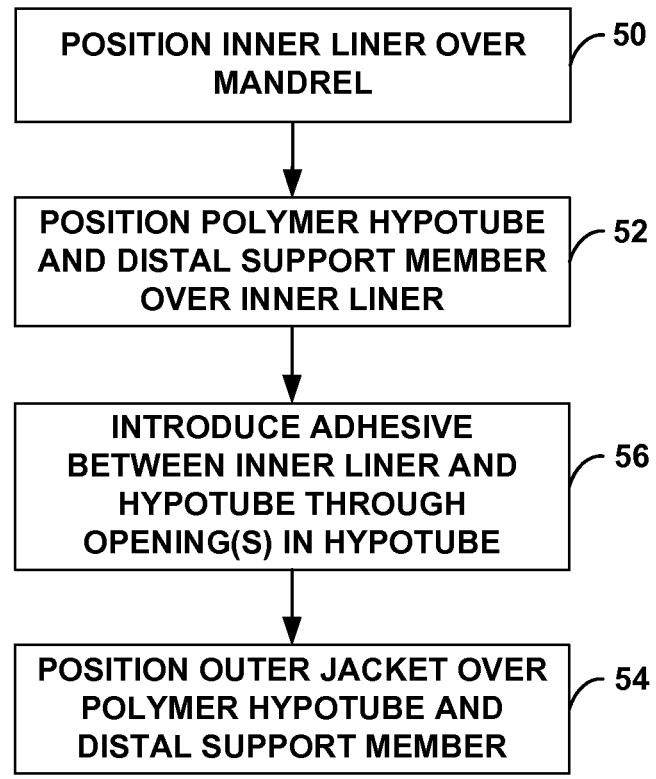

FIG. 7 is flow diagram of another example method of forming a catheter. Although FIG. 7 is described with reference to catheter body 40 shown in FIG. 5, in other examples, the technique shown in FIG. 7 may be used to form another catheter body. The method shown in FIG. 7 is similar to the method described with respect to FIG. 6, but includes introducing an adhesive between inner liner 32 and polymer hypotube 42 via one or more openings 44 defined by polymer hypotube 42 (56). The method may further include curing the adhesive prior to or after positioning outer jacket 20 over polymer hypotube 44 and distal support member 26 (54).

The method shown in FIG. 7 may further involve defining a plurality of openings 44 in a longitudinally-extending wall of polymer hypotube 42. Openings 44 may be defined by laser drilling openings into the longitudinally-extending wall of polymer hypotube 42, though other methods of drilling may be used. As Openings 44 may be defined to have other shapes, arrangements, and sizes not specifically disclosed herein.

In some examples, catheter 10, catheter body 12, and/or catheter body 40 may be a part of an assembly that includes, e.g., a guidewire and/or another catheter. The catheter 10, catheter body 12, and/or catheter body 40 in such an assembly can be any of the examples of catheters or catheter bodies disclosed herein. The guidewire may be used to guide catheter 10 to a target tissue site within the vasculature of a patient. In addition, in some examples, the additional catheter of the assembly may also be configured to guide catheter 10, catheter body 12, and/or catheter body 40 to a target tissue site within the vasculature of a patient. The additional catheter of the assembly may be substantially similar (e.g. identical or nearly identical) in construction to catheter 10 (including any of the examples of the catheter 10 disclosed herein), but may have proportionally greater or smaller dimensions, such that the catheter bodies of the catheters may nest together. The assembly may therefore comprise the catheter 10 with the additional catheter positioned in the inner lumen 34 of the catheter, and may further comprise the guidewire positioned in the inner lumen of the additional catheter.

Each of the components of the assembly may be slidably disposed relative to the other(s) so that each may be advanced and/or retracted over or within the other(s). For example, when the additional catheter is positioned in lumen 34 of the catheter 10, the catheter 10 may be advanced or retracted longitudinally over the additional catheter, and/or the additional catheter can be advanced or retracted longitudinally within the catheter 10. The use of the additional catheter in this manner may help reduce any adverse interactions with tissue attributable to the ledge effect, as can occur when a relatively large catheter is advanced over a guidewire through a curve in a vessel and the distal rim of the catheter scrapes the vessel wall on the "outside" of the curve. For example, if in use of an assembly having a guidewire the guidewire is first advanced into the vasculature, the additional catheter may next be advanced over the guidewire before the catheter 10 is advanced over the additional catheter. The difference in outer diameter between the guidewire and the additional catheter (and between the additional catheter and the catheter 10) is less than the difference in outer diameter between the guidewire and the catheter 10. Therefore, any ledge effect arising from advancing the catheter 10 over a "bare" guidewire may be mitigating by use of the additional catheter in this manner. In other examples, the additional catheter of the assembly may have a larger outer diameter than catheter 10 or body 12 and may be guided over catheter 10 or body 12 to a target tissue site within the vasculature of the patient.

In some examples, a method of using a catheter described herein comprises introducing a guidewire or inner catheter into vasculature (e.g., an intracranial blood vessel) of a patient via an access point (e.g., a femoral artery) and guiding distal end 12B of catheter body 12 over the guidewire or inner catheter to the treatment site. Once distal end 12B of catheter body 12 is positioned at the target tissue site, diagnostic agents, therapeutic agents, devices, or other objects may be delivered via hub 14, through inner lumen 34, and to the treatment site via distal opening 10B.

Various examples have been described. These and other examples are within the scope of the following claims.

What is claimed is:
1. A catheter comprising:
    a catheter body comprising:
        an inner liner;
        a generally tubular outer jacket; and
        a structural support member positioned under the outer jacket and around the inner liner, the structural support member comprising a monolithic proximal polymer hypotube and a distal braided or coil member that is more flexible than the monolithic proximal polymer hypotube, wherein the monolithic proximal polymer hypotube ends proximal to a proximal end of the distal braided or coil member and the distal braided or coil member is longitudinally adjacent to the monolithic proximal polymer hypotube, and wherein the monolithic proximal polymer hypotube extends along 20% to 50% of a total length of the catheter body.

2. The catheter of claim 1, wherein the monolithic proximal polymer hypotube comprises polyether ether ketone (PEEK).

3. The catheter of claim 1, wherein the monolithic proximal polymer hypotube has a wall thickness of about 38.1 microns to about 63.5 microns.

4. The catheter of claim 1, wherein the monolithic proximal polymer hypotube has a stiffness of about 11.5 gram-force centimeter to about 460 gram-force centimeter.

5. The catheter of claim 1, wherein the monolithic proximal polymer hypotube has a varying wall thickness.

6. The catheter of claim 1, wherein the monolithic proximal polymer hypotube has a sidewall which is uncut along its length.

7. The catheter of claim 1, wherein a distal end of the monolithic proximal polymer hypotube and the proximal end of the distal braided or coil member longitudinally abut each other.

8. The catheter of claim 1, wherein the monolithic proximal polymer hypotube is positioned around a proximal portion of the inner liner and the distal support member is positioned around a distal portion of the inner liner.

9. The catheter of claim 1, wherein a longitudinally-extending wall of the monolithic proximal polymer hypotube defines a plurality of openings.

10. The catheter of claim 9, wherein the inner liner defines an inner lumen of the catheter, wherein the monolithic proximal polymer hypotube is positioned over at least a portion of the inner liner, and wherein the catheter body further comprises:
an adhesive positioned between at least a portion of the inner liner and at least a portion of the monolithic proximal polymer hypotube, wherein the adhesive extends at least partially through at least one opening of the plurality of openings.

11. The catheter of claim 1, wherein the proximal portion of the catheter body is devoid of the distal braided or coil member.

12. The catheter of claim 1, wherein one of:
the distal braided or coil member is in direct radial contact with the inner liner and the generally tubular outer jacket; or
only an adhesive is disposed between at least one of: the distal braided or coil member and the inner liner or between the distal braided or coil member and the generally tubular outer jacket.

13. The catheter of claim 1, wherein one of:
the monolithic proximal polymer hypotube is in direct radial contact with the inner liner and the generally tubular outer jacket, or
only an adhesive is disposed between at least one of: the monolithic proximal polymer hypotube and the inner liner or the monolithic proximal polymer hypotube and the generally tubular outer jacket.

14. A catheter comprising:
a catheter body comprising:
an inner liner defining an inner lumen of the catheter;
a monolithic proximal polymer hypotube positioned over at least a portion of the inner liner, wherein a longitudinally-extending wall of the monolithic proximal polymer hypotube defines a plurality of openings;
an adhesive positioned between at least a portion of the inner liner and at least a portion of the monolithic proximal polymer hypotube, the adhesive extending at least partially through at least one opening of the plurality of openings; and
a distal braided or coil member that is more flexible than the monolithic proximal polymer hypotube, wherein the monolithic proximal polymer hypotube ends proximal to a proximal end of the distal braided or coil member and the distal support braided or coil member is longitudinally adjacent to the monolithic proximal polymer hypotube.

15. The catheter of claim 14, wherein the monolithic proximal polymer hypotube has a stiffness of about 11.5 gram-force centimeter to about 460 gram-force centimeter.

16. The catheter of claim 14, wherein the openings each have a diameter of about 0.1 millimeters to about 0.8 millimeters.

17. A method of forming a catheter, the method comprising:
positioning a monolithic proximal polymer hypotube and a distal braided or coil member around an inner liner and adjacent to each other along a longitudinal axis such that the monolithic proximal polymer hypotube ends proximal to a proximal end of the distal braided or coil member, the distal braided or coil member being more flexible than the monolithic proximal polymer hypotube; and
positioning an outer jacket over the monolithic proximal polymer hypotube and the distal braided or coil member, wherein a proximal portion of the catheter comprises the monolithic proximal polymer hypotube and a distal portion of the catheter comprises the distal braided or coil member, wherein the monolithic proximal polymer hypotube extends along 20% to 50% of a total length of the catheter body.

18. The method of claim 17, wherein positioning the monolithic proximal polymer hypotube and the distal braided or coil member adjacent to each other comprises:
positioning the inner liner over a mandrel;
positioning the monolithic proximal polymer hypotube over a proximal portion of the inner liner; and
positioning the distal braided or coil member over a distal portion of the inner liner longitudinally adjacent to the monolithic proximal polymer hypotube.

19. The method of claim 17, further comprising defining a plurality of openings in a longitudinally-extending wall of the monolithic proximal polymer hypotube.

20. The method of claim 19, further comprising, after defining the plurality of openings:
introducing an adhesive between the monolithic proximal polymer hypotube and the inner liner through at least one opening of the plurality of openings.

21. The method of claim 20, wherein introducing an adhesive between the monolithic proximal polymer hypotube and the inner liner through at least one opening of the plurality of openings comprises injecting the adhesive through the at least one opening with a syringe.

* * * * *